United States Patent
Tamil et al.

(10) Patent No.: US 9,161,705 B2
(45) Date of Patent: Oct. 20, 2015

(54) METHOD AND DEVICE FOR EARLY DETECTION OF HEART ATTACK

(75) Inventors: Lakshman S. Tamil, Plano, TX (US);
Mehrdad Nourani, Plano, TX (US);
Gopal Gupta, Plano, TX (US); Subhash Banerjee, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 287 days.

(21) Appl. No.: 13/314,043

(22) Filed: Dec. 7, 2011

(65) Prior Publication Data

US 2012/0179055 A1 Jul. 12, 2012

Related U.S. Application Data

(60) Provisional application No. 61/420,668, filed on Dec. 7, 2010.

(51) Int. Cl.
*A61B 5/0402* (2006.01)
*A61B 5/0452* (2006.01)
*A61B 5/00* (2006.01)

(52) U.S. Cl.
CPC ............. *A61B 5/0452* (2013.01); *A61B 5/726* (2013.01); *A61B 5/7465* (2013.01)

(58) Field of Classification Search
CPC ..... A61B 5/0452; A61B 5/7465; A61B 5/726
USPC .......................................................... 600/509
See application file for complete search history.

(56) References Cited

U.S. PATENT DOCUMENTS

| | | | | |
|---|---|---|---|---|
| 5,626,629 | A * | 5/1997 | Faltys et al. | 607/57 |
| 2005/0131477 | A1* | 6/2005 | Meyer et al. | 607/27 |
| 2005/0203352 | A1* | 9/2005 | Al-Ali et al. | 600/309 |
| 2007/0265533 | A1* | 11/2007 | Tran | 600/481 |
| 2009/0240157 | A1* | 9/2009 | Lian et al. | 600/510 |

* cited by examiner

*Primary Examiner* — Alyssa M Alter
(74) *Attorney, Agent, or Firm* — Winstead PC

(57) ABSTRACT

A device and method for heart performance characterization and abnormality detection is disclosed herein. The device and method analyze and characterize cardiac electrophysiological signals which help in the diagnosis of myocardial ischemia in advance of a heart attack.

16 Claims, 8 Drawing Sheets

LIFTING SCHEME (LWT)

UNDECIMATED LIFTING SCHEME (ULWT)

METHOD AND DEVICE FOR EARLY DETECTION OF HEART ATTACK

CROSS REFERENCES TO RELATED APPLICATIONS

This application claims the benefit under 35 U.S.C. 119(e) of U.S. Provisional Patent Application Ser. No. 61/420,668 filed Dec. 7, 2010, which is incorporated herein by reference in its entirety as if fully set forth herein.

FIELD OF THE INVENTION

The invention is directed to methods and devices that provide an early warning of impending heart problems thereby providing the user with the ability to seek medical intervention before there is irreversible damage.

BACKGROUND OF THE INVENTION

Identifying acute myocardial infractions early on and treating them promptly significantly improves the clinical outcomes. Studies have shown that the most irreversible myocardial damage occurs in the first 30 to 90 minutes of coronary occlusion. It has been demonstrated that providing reperfusion therapy within two hours of occlusion has the greatest chance to save the myocardium. Also, evidence exists that even in cases of the most severe type of myocardial infarction (MI) called ST elevation MI (STEMI), rapid restoration of blood supply after onset of symptoms is a key factor in determining the short and long term outcomes. Therefore, it is very clear that early arrival at the hospital for prompt diagnosis and treatment is the key to increasing the odds of a better outcome.

Despite wide-spread public campaigns and education on this matter, the average time for a patient to reach the hospital from the onset of the symptoms is more than three hours in urban areas and can be longer than 20 hours in rural areas. The cause of the delay is mostly due to the ignoring or the misconception of the symptoms experienced by the patient and their confusion with their attributes. Most of the heart attacks are silent and cause little to no pain. In case of diabetic patients, it is even worse because they do not feel the attack at all. FIG. 1 is a schematic representation that captures the overall view of the American Heart Association regarding the delay in symptom recognition and reaching the hospital as the leading causes of death in coronary heart diseases (both sudden cardiac deaths and heart attacks). This scenario clearly states the need for a device that can warn the patient when they go through the myocardial infarction and prompts them to seek immediate attention. Such a device can save lives and can also save billions of dollars in costly after care treatment.

Taking a look at the current state of the art in surveillance of coronary heart diseases, the options available are (i) 12 lead ECG machines, which are not portable and mostly available in hospital settings; (ii) Holter machines, which have no real time prediction capability to forewarn an impending heart attack; (iii) Contemporary monitoring solutions that can detect only simple arrhythmias by measuring RR intervals and cannot detect impending heart attacks because lethal arrhythmias are presented after the start of the attack; and (iv) implantable devices that can monitor ST-elevation or depression and provide warning. The drawback of the implantable device is that it requires surgery and caters only to the high risk population.

Clearly none of the options set forth in the above list can satisfy the current unmet need, i.e., an accurate early warning system for heart attack and sudden cardiac death. Such an early warning system should also be capable of being used easily and by a larger segment of the public. The claimed invention is directed to the development of such a method and device.

SUMMARY OF THE INVENTION

An aspect of the invention is directed to a device for heart performance characterization and abnormality detection, comprising: an interface for receiving sampled data representing an electrical signal indicating electrical activity of a patient heart over a plurality of heart beat cycles; a signal processor for using the received sampled data in determining a first ECG morphological signal over a plurality of heart cycles; a comparator for comparing the first ECG morphological signal value with a threshold value to provide a comparison indicator; and a patient monitor that in response to said comparison indicator indicates a calculated signal characteristic value exceeding the threshold value, and generates an alert message associated with the threshold. In certain embodiments, the alert message is communicated to a user via a smartphone. In other embodiments of the invention, the computation of abnormality is carried out via a device such as a smartphone.

Another aspect of the invention is directed to a method for heart monitoring, characterization and abnormality detection, comprising the activities of: acquiring an electrophysiological signal representing a heart beat cycle of a patient heart; identifying a change in ST slope (ST deviation) or T wave (T wave deviation), and correlating the change in the ST slope or T wave to an imminent cardiac event. In certain aspects of the invention, a change in both the ST slope and T wave is identified concurrently.

DETAILED DESCRIPTION OF EXEMPLARY EMBODIMENTS

Sudden Cardiac Death (SCD) is an unexpected death caused by loss of heart function when the electrical impulses fired from the ventricles become irregular. Most common SCDs are caused by cardiac arrhythmias and coronary heart disease is one of the main risk factors for SCD cases. They occur mainly due to myocardial ischemia and the subsequent Acute Myocardial Infarction (AMI) and cardiac arrhythmia. An embodiment of the claimed invention aims to automate the recognition of ST-segment deviations and transient ST episodes which help in the diagnosis of myocardial ischemia in advance and also aid in classifying major cardiac arrhythmia.

Figure 1:
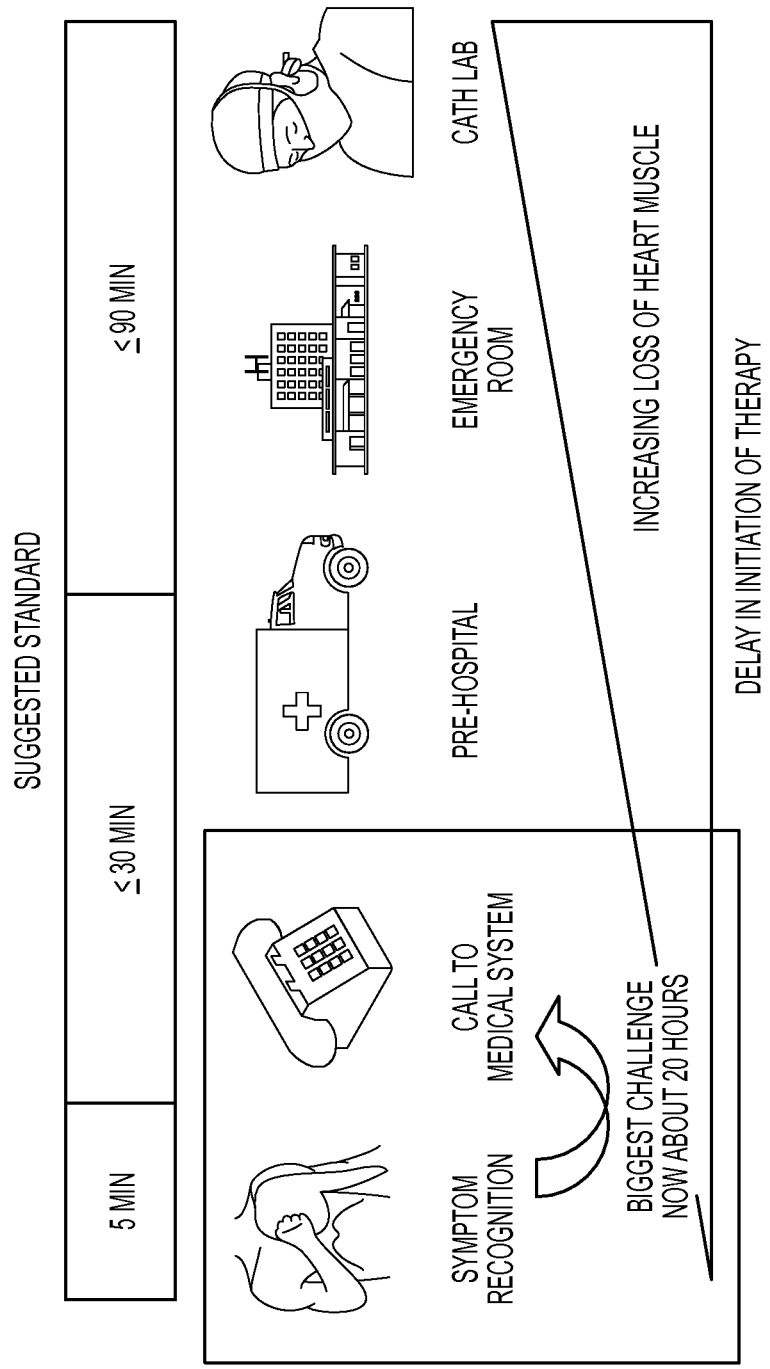
FIG. 1 is a schematic drawing that illustrates the importance of early detection of cardiac arrhythmia as set forth by the American Heart Association.
Figure 2:
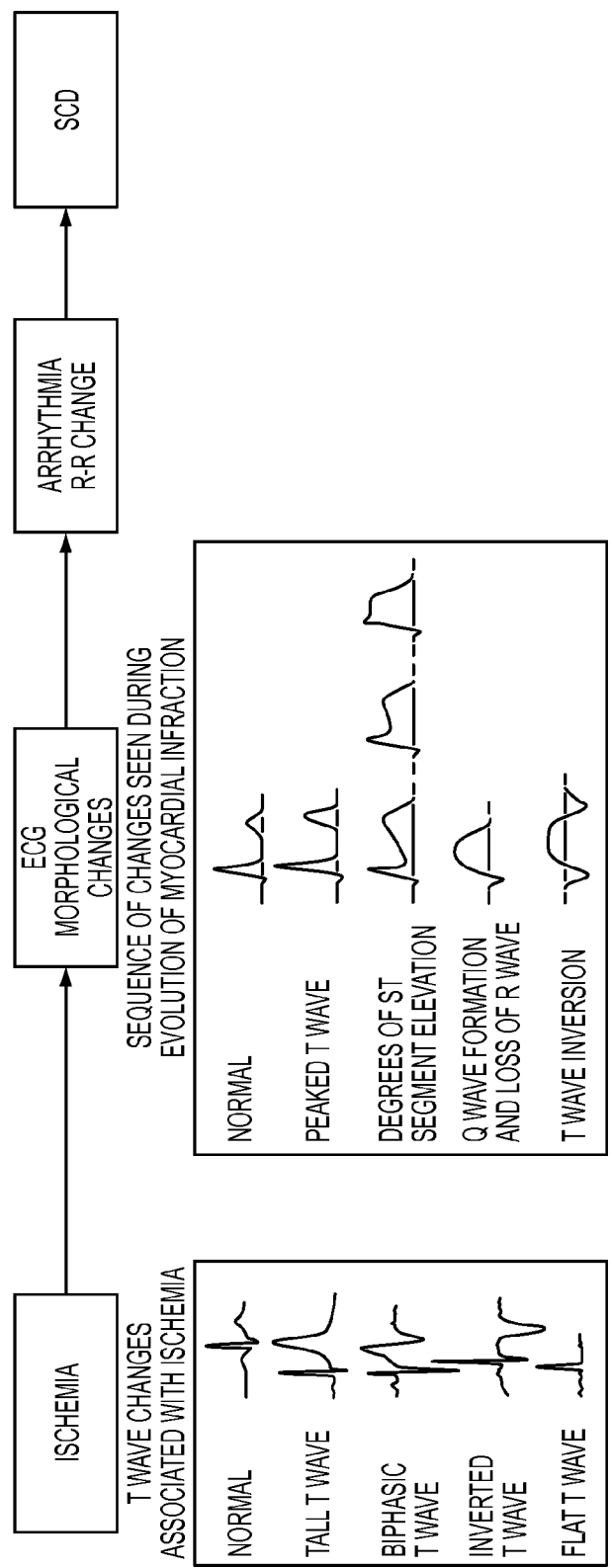
FIG. 2 shows the sequence of changes in the ECG morphology during evolution of myocardial infarction.

FIG. 2 shows the sequence of changes in the electrocardiogram (ECG) morphology during evolution of myocardial infarction. The earlier the problem can be detected, the more time there is to save the person. Looking at FIG. 2, it can be seen that there is more value to detecting the early morphological changes in ECG than the arrhythmia. Detecting arrhythmia is easier but of lesser value because lethal arrhythmia often occurs after the presentation of heart attack, by which time it may be too late for the person.

An embodiment of the invention is directed to the accurate detection and classification of the morphological changes in ECG in real time and with lesser computational complexity than is currently available in the state of art. A further embodiment of the invention allows a user to obtain information pertaining to morphological changes in ECG via the user's smartphone. In this embodiment, the user wears an ECG sensor and the sensor in combination with software that is downloaded to the user's smartphone, serves as a heart attack monitor that can monitor him continuously anywhere, anytime and provides relevant alerts in the event of an impending heart attack.

Figure 3:
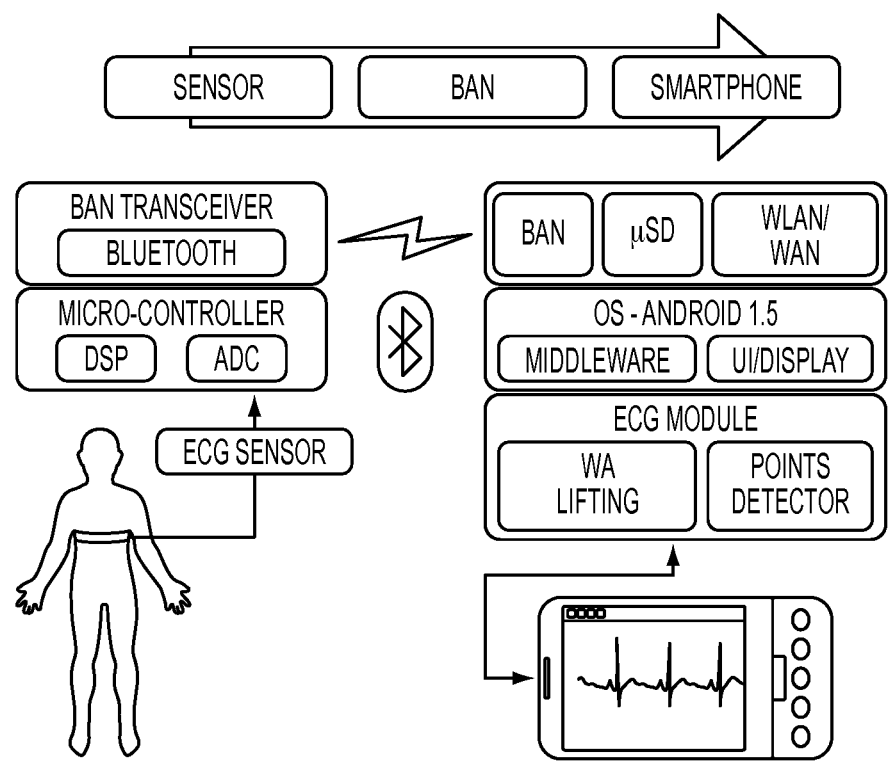
FIG. 3 shows real time ECG analysis and monitoring in accordance with an embodiment of the invention.

As previously stated, in an embodiment of the invention, the smartphone may be used to alert a user in accordance with the principles of the claimed invention (see FIG. 3). The smartphone is becoming the favorite connected computing platform of the masses. It has a large customer base, ease of portability, small footprint, is cheaper and is more ubiquitous than laptops and PCs. The smart phone that has become the multifaceted gadget can also play the role of a modern physician assistant. The ubiquitous connectivity it can offer and the tremendous processing power available in today's smart phones make it an excellent candidate to play the role of a physician assistant. Modern information technology that has brought scalability and cost reduction to many other industries can now bring the same to the healthcare. The essentiality to provide universal healthcare and at the same time reduce the escalating healthcare cost is a challenge that many nations are facing and the system like the one proposed here is clearly a winning step towards facing the challenge. In certain embodiments of the invention, the computation is carried out by the smartphone or other similar device.

An embodiment of the invention provides a method and device for modeling morphological changes for real time prediction and learning an accurate model for coronary disease classification.

A detection algorithm is capable of detecting accurately all of the QRS complex, ST-complex, QT interval, T wave and T-wave alternans (TWA), either individually or in combination. Using different mathematical techniques for each of the segment makes the system computationally very complex and inapplicable for real time applications. A better mathematical technique that can detect all the segments accurately in order to provide a unified scheme for detecting all ECG morphological changes is a wavelet via lifting scheme that has been developed and tested.

The ST-segment is transient in nature and there is a wide variation in the amplitude of the ST-segment due to non-ischemic conditions such as drift, change in electrical-axis of the heart and changes in ventricular conditions in addition to ischemia. Time varying reference level set by the non-ischemic conditions need to be tracked in order to accurately determine the ST-segment. Transient ST-segment episodes are the few intervals during which an abnormal/crucial ST elevation is observed. As they occur as bursts in a short interval of time, they are called episodes. These episodes vary anywhere between one minute to several minutes and they do not persist for long hours together. An accurate detection of these transient ST-episodes is crucial to the accuracy of the system. The detection of TWA is also difficult owing to small rate of change in morphology of the T-wave.

An embodiment of the invention is directed to a method for heart monitoring, characterization and abnormality detection, comprising the activities of: acquiring an electrophysiological signal representing a heart beat cycle of a patient heart; identifying a change in ST slope or T wave, and correlating the change in the ST slope or T wave to an imminent cardiac event. In certain aspects of the invention, a change in both the ST slope and T wave is identified concurrently.

An embodiment of the claimed invention is directed to the development of a model for determining whether there is an abnormality in the heart beats of a subject being monitored, so that the system can provide an early warning when the abnormality is observed. In this embodiment, machine learning is employed to combine information extracted from the automatically detected ST-segments, QT interval and T wave and other knowledge sources to build an accurate Coronary Heart Disease (CHD) classifier. First, to achieve high accuracy, a personalized prediction model must be built for the patient who is to be monitored. However, this requires an optimal way to combine the data collected from one patient with the data obtained from standard databases to create the model. Second, unlike many standard classification tasks where the underlying data set is unchanged over time, the data is collected from the patient in real time. In particular, the data points in the data stream are not independent of each other, and recently-collected data points may be more informative than those collected in the more distant past. Thus, it is necessary to build a "time-aware" model that can capture the relationship among the data points with respect to time? Finally, given that a smartphone-type device has limited processing power and memory, it would be desirable to use a simple prediction that can be trained and applied efficiently, but without sacrificing accuracy.

Figure 4:
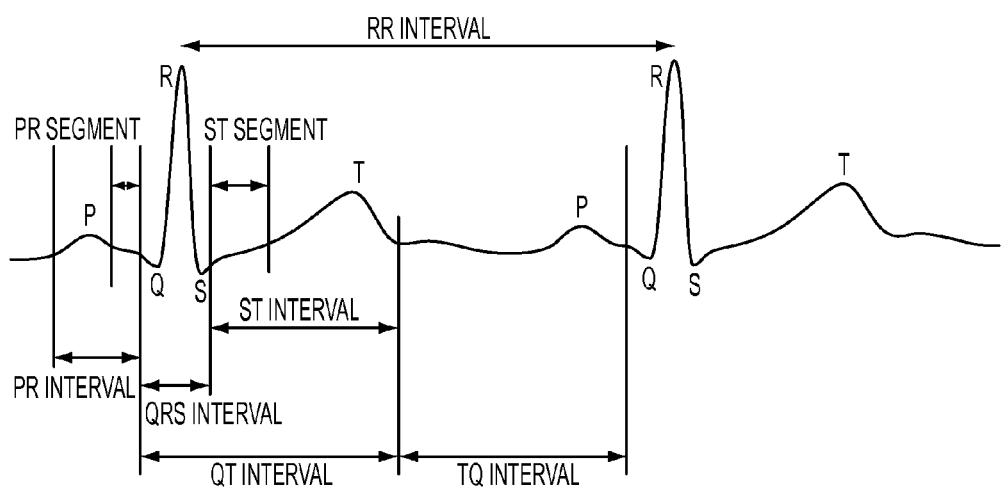
FIG. 4 shows a sample two cycle ECG recording with fiducial points marked.

The Electrocardiogram (ECG) is the most widely adopted clinical tool to diagnose and assess the risk of cardiovascular diseases. ECG is an electrical recording of the heart behavior and is crucial to investigating cardiac abnormalities. Each beat is an electrical impulse travelling through the heart, which causes the muscle to squeeze and pump blood. FIG. 4 shows a two cycle ECG recording with the fiducial points of importance; P wave, QRS complex and ST-T complex. The first indication of shortage of blood supply to the heart muscles (myocardial ischemia) shows up in the ECG as transient changes in the T waves, immediately followed by changes in the morphology of the ECG (ST-complex, QT interval, QRS-complex) and later followed by arrhythmia which are changes in the RR interval. In cases of ventricular arrhythmia that cause sudden cardiac death, when arrhythmia is observed, it is already too late to save the person. The opportunity to save the person still exists if morphological changes in the ECG can be detected sooner rather than later. In particular, it is best if the transient change in the T wave that happens right after ischemia is detected as soon as it occurs (See FIG. 2).

The ECG recordings are typically examined visually by a physician for important features. Nowadays automated ECG diagnosis helps the physicians in reducing the error and arriving at the correct diagnosis quicker. These automated ECG analysis tools are offline tools. In circumstances where the ECG can be used as an early warning tool for cardiac attacks or sudden cardiac arrests, automated offline tools are of no use. What is needed is a real-time tool that can assess every beat and pick up the anomaly. Among the morphological changes in ECG, the one that can give an early indication as well as more information is the change in ST-segment (elevation or depression). Although a lot of work has been done in the area of detecting and analyzing RR intervals, it has limited value. The claimed invention is directed to the detection of changes in the morphology of the ECG and the classification of these changes to arrive at a diagnosis. Among the ECG morphological changes, the claimed invention is directed towards assessing ST-segment, QT interval and T wave, either singly or in combination.

An embodiment of the invention is directed to the development of real time processing capable algorithms. Additionally, the various sections of the ECG morphology are analyzed using various different mathematical techniques. While it may not be possible to use a simple smart phone or a hand-held device to detect all of these segments, a unified technique that can accurately analyze the changes in all the segments is one of the goals of the claimed invention.

The differentiation as to whether the changes in the ECG morphology are due to an ischemic event or due to a non-ischemic event, though very difficult, is very important in developing any early warning tools having low false alarm. Such differentiation as well as accurate automated diagnosis of the coronary heart disease is possible only if an efficient classifier is developed that can look at the various features and classify them into various diagnostic groups with very little error. The accuracy of these classifiers can be enhanced if a personalized feature set in addition to the global feature set is used in the design of the classifier.

Wavelet multiresolution analysis is a proven powerful tool for many biomedical signal processing applications such as data compression, denoising and feature detection. Wavelet transform decomposes the signal into various components that appear at different scales. It also uses a linear operation which makes it suitable to preserve the important phase information of the signal. Traditional wavelet analysis is already used in electrocardiogram (ECG) signal pre-processing, detection of characteristic points and feature extractions. The claimed invention provides properties to meet realtime processing criteria, e.g. speedup and reduced memory footprint, which satisfy medical embedded applications requirements such as low power consumption, low processing power and low memory usage.

In an embodiment of the claimed invention, the claimed invention consists of two modules. A first module provides a measurement of change of St-segment, QT interval or T wave and episode detection which is of major significance in Ischemia detection. This uses wavelet transform based signal processing.

In an embodiment of the invention, a second module classifies the heart beats into normal and five different commonly observed arrhythmia classes commonly observed by cardiologists. The second module uses supervised learning algorithms that are specifically designed for the claimed system. The algorithms are capable of classifying hearts beats under the following classifications: premature ventricular contraction (V), premature atrial contraction (A), fusion (F), right bundle branch block (R), left bundle branch block (L) and normal (N). The ST-segment analyzer provides an accuracy of 98.57% in ST-recognition, 97.34% in ST-deviation measurement and 93.33% in ST-episode detection. The beat classifier provides an overall high accuracy of 96.35% in classifying the six classes of heart beats.

To identify the ST-segment in an ECG signal, accurate detection of the isoelectric line, the J point and the heart rate are required. The isoelectric line is the baseline of the electrocardiogram, typically measured between the T wave offset and the preceding P wave onset. It indicates no muscular activity in the heart at a particular point of time. This line is used as a reference to measure ST-segment deviation. The J point is the inflection point at which the QRS complex changes its direction of propagation. It occurs after the offset of the QRS point within a window of 20-50 samples at the rate of 250 Hz of sampling. The isoelectric point, the QRS offset and the J point are detected by discrete wavelet transform.

Discrete Wavelet Transform (DWT) which is of great importance in analyzing biomedical signals, represents the ECG signal in both time and frequency domains through time windowing function.

The length of the window indicates a constant time and frequency resolution. The wavelet transform decomposes the ECG signal into different scales with different levels of resolution by scaling it to a single prototype which has a zero net area, called the mother wavelet. DWT makes use of multi-resolution analysis which enables the signal to be analyzed in different frequency bands by passing the signal into cascaded levels of high-pass and low-pass filters, resulting in detailed and approximate coefficients. The level at which the coefficients are obtained is called scale, represented as $2^n$ for n-stage/level filtering.

In an embodiment of the invention, a single UWLT (Undecimated Wavelet Transform) Decomposition is implemented with Db4 (Daubechies) as the mother wavelet. The level is determined based on the frequency sub-band to be extracted from the ECG signal. The transform is applied at the scales of $2^3$ and $2^1$. The isoelectric line is determined by approximating each beat with the $2^3$ scale transform. A search method is used to find the most stable zero crossings between the P and T waves. This is obtained by using the windowing and backward search algorithms for the signal before the QRS complex. This is repeated for 20 beats and the average is determined as the isoelectric line.

The J point is detected from the $2^1$ scale transformation. This point corresponds to the peak after the S point. On estimating the J point, the ECG inflection point is determined on the denoised signal before applying transformation.

The ST-segment is defined as the part of the ECG signal between the J point and the onset of the T wave. This is achieved by the Windowing Technique. On the $2^1$ scale, a windowed search is implemented from the S point. The region where the slope of the signal is maximum is determined and a backward search starts from the local maximum till the point where the signal is minimal. This point is fixed as the T onset. If there is no local maximum or minimum in the windowing technique, the T onset is estimated to be at the J+80 point.

The heart beat classification system of the invention is implemented by the Support Vector Machine approach. It is a supervised learning framework which performs classification by constructing an N dimensional hyper-plane that optimally separates the data into two categories. It is one of the best learning algorithms that gives the flexibility for the choice of the kernel and performs training in less time when compared to other learning algorithms like neural networks. Every heart beat is represented as a row in the data set with its feature values and its class label. SVM aims to find the optimal separating plane and the data points that determine the position and the orientation of the plane are called the support vectors.

The system is designed to classify six major arrhythmia most commonly observed by the cardiologists.

In an embodiment of the invention, two types of features are used to describe each heart beat Or one cardiac cycle: 1. Morphological Features and 2. DWT Features.

The invention uses 12 morphological features that provide the timing, area, energy and correlation information of the signal. The inventive method uses the ST-segment features, viz. the slope of the ST-segment, the ST-deviation measurement and the correlation coefficients of the signal with the templates of each class. Each class is represented by a template manually chosen from the MIT-BIH database. The correlation coefficient lies between 0 and 1; the higher the coefficient is, the more likely it is for the signal to belong to that class.

The twelve morphological features used in embodiments of the invention are: (i) QS Width, (ii) Pre RR Interval, (iii) Post RR Interval, (iv) QR Width, (v) RS Width, (vi) Mean Power Spectral Density, (vii) Area Under QR, (viii) Area Under RS, (ix) Autocorrelation Value, (x) ST-segment Deviation, (xi) Slope of ST; and, (xii) Correlation coefficient with class template.

Embodiments of the invention use 191 DWT (Discrete Wavelet Transform) coefficients, which are obtained by a 4 level decomposition of the signal with the db2 mother wavelet. These coefficients are based on the 180 samples taken to represent each heart beat. These are a good representation of the signal in frequency and time domains. We train six classifiers, each for identifying one arrhythmia type and using all the heart beats in our databank for training and testing. The six single beat classifiers are: N vs. All, V vs. All, A vs. All, L vs. All, R vs. All and F vs. All.

Each data sample (heart beat) is represented by its class label and all 191+12=203 feature values, including the morphological and DWT features. Since five-fold cross validation experiments are performed, four folds of the data are used for training the classification system. In particular, six classifiers are trained, one for identifying a particular type of beat using the one-versus-all scheme, resulting in six binary beat classifiers. After training, the test data set from the remaining fold (i.e., the fold not used for training) is given to the classification system. The classification is a two stage process. During the first stage, the training data is generated with the features selected. In the present invention, the ECG beats are divided into five sets of equal number of beats. One out of the five sets is randomly selected and labeled as Test Data Set. The remaining four sets are labeled as Training Data Sets and are passed into the feature extraction module where each beat is represented with the 203 features. The sets thus obtained are used to train the learning algorithm, SVM, which results in a SVM model file containing all the beats which form the hyper plane for classification. In the second stage, the SVM model file and the Test Data Set are given as the input to the SVM classifier tuned to the selected parameters. The output of the classifier gives the prediction of the class for each beat in the Test Data Set. This process is repeated with every data set as the Test Set and with different Classifier parameters. The final class prediction is determined based on the highest prediction value of the SVM for the specific beat.

Several techniques such as maximum likelihood, (artificial) neural networks, and support vector machines have been introduced for ECG beat classification. These machine learning techniques map new data in-stances based on the information extracted from the annotated training data in the learning phase. Most techniques provide a global classifier that may not be always accurate for patient-specific cardiac variations. Automated arrhythmia diagnosis systems that can provide high classification accuracy rates for inter and intra-patient variation cases are still an active area of research.

Figure 8:
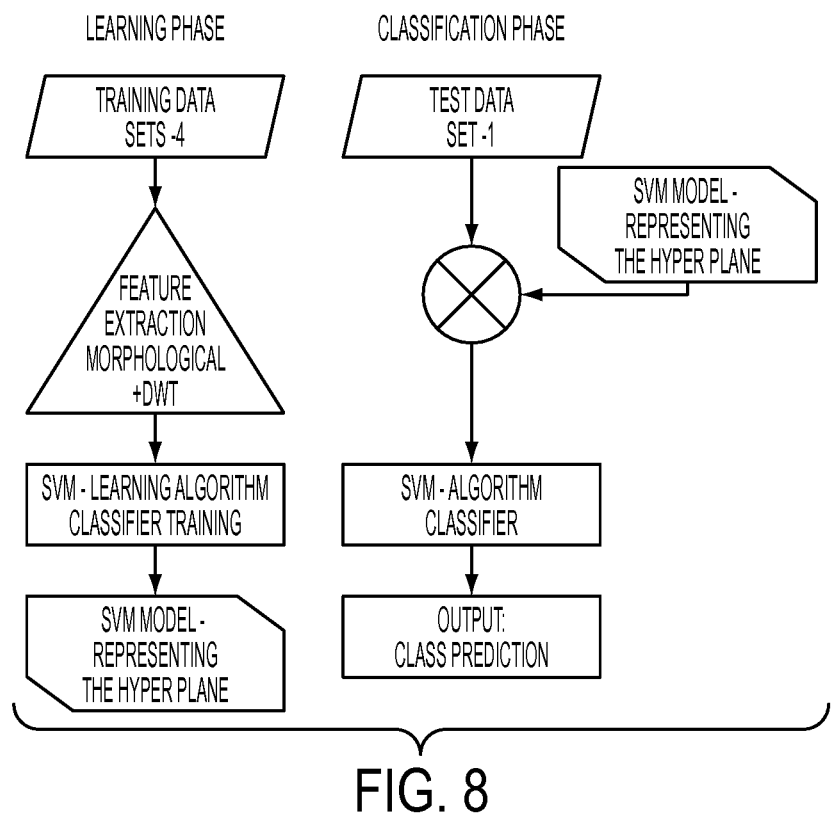
FIG. 8 is a schematic illustration of the working principles of a beat classifier.
Figure 9:
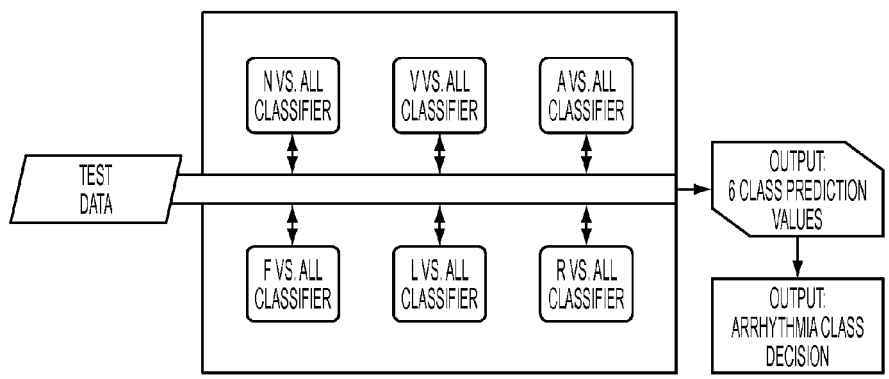
FIG. 9 shows a flowchart of a process used by a system for cardiac abnormality detection, according to principles of the invention.

FIG. 8 is a schematic illustration of the working principles of a beat classifier and FIG. 9 shows a flowchart of a process used by a system for cardiac abnormality detection, according to principles of the invention.

Support Vector Machines (SVM) have been around for quite some time and have grabbed much attention for ECG beat classification. In this technique, training data sets with known classes are given to the SVM program. Based on the training data, SVM determines hyperplanes in the feature space for each class. The distances between the features of each instance and hyperplanes (classes) are computed and the hyperplane holding the minimum distance indicates that the instance is of that particular class. Each instance of data in SVM contains important features of the heart beat. For example, the instances of an SVM may contain QRS duration, RR interval, amplitude of P, Q, R, S and T points. In other words, each instance is a vector of certain features of a beat, often called feature vector. SVM methods provide good classification results using less training data sets and small feature vector sizes.

In beat classification using the SVM method, various ECG features may have information about different classes (types) of coronary artery disease.

Apart from SVM, other classification techniques have been also studied such as a knowledge-based method for arrhythmic beat classification, arrhythmic episode detection and classification using only the RR-interval signal; a learning algorithm for analyzing the gray relations between templates and test data set; and analyzing the RR intervals and ECG morphology features along with heart beat segmentation information.

Artificial neural networks along with the mixture of experts (MOE) approach is a technique that uses a local classifier in addition to a global classifier in order to classify ECG beats. This technique is quite effective since a crisp global classifier that clearly defines a normal region for ECG features in a beat does not exist. Rather, a local classifier more or less particular to each individual is required to accurately classify the beats. A modified mixture of experts (MME) approach has been used in which a higher classification accuracy compared to MOE and many artificial neural networks schemes is gained. Pathological cardiac events are identified using a patient-adaptive classifier that analyzes the deviation of the RR interval from the mean value, and the deviation of QRS patterns from the sustained rhythm.

Most of the work so far on ECG signal analysis and classification focus on offline processing, while real-time monitoring and early detection has remained a challenge until now. Hardware engines customized for ECG analysis allow real-time processing and detection. Hardware configuration for an ECG monitoring device and the detection of ST pattern change has been described. FPGA-oriented systems have also been introduced that allow real-time monitoring and analysis of ECG beats. These systems gain high processing speeds by the help of hardware concurrency. Thus, an aim of the claimed invention is to design a low-power, high performance early warning system that can perform online processing on a handheld smart phone or other suitable portable device.

Second generation wavelets via lifting schemes can provide denoising, detrending and characteristics points detection for all segments of ECG morphology using just one decomposition phase. This and other advantages it offers like its real-time capability and reduced memory footprint make it an excellent candidate for smart phone or hand held applications. The lifting scheme or the second generation wavelets is a novel way of looking at the construction of biorthogonal wavelets. The basic idea of second generation wavelets is to abandon translation and dilation to construct wavelets. The lifting scheme allows the generation of an infinite number of discrete biorthogonal wavelets starting from an initial one. Selecting the "Lazy" wavelet leads to a trivial initial set of biorthogonal filters.

Figure 5A:
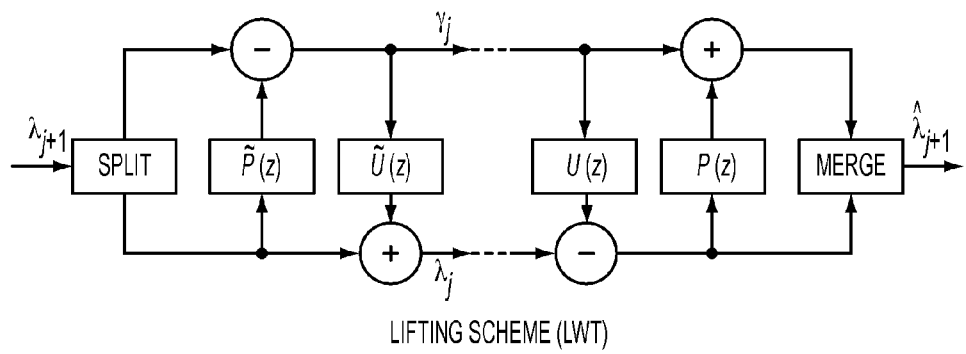
FIGS. 5A and 5B illustrate lifting schema implementations of fast wavelet transform.

Lifting operations involves applying a finite sequence of primal or dual Elementary Lifting Steps (ELS). A dual ELS is lifting the high-pass subband with the help of the low-pass subband, while primal ELS is lifting the low-pass subband with the help of the high-pass subband. The three lifting stages shown in FIG. 5A uses the operators: Split referring to "Lazy" wavelet, Predict operator (P) refers to "dual" ELS, and Update operator (U) referring to "primal" ELS. Iterating the lifting scheme to the nth decomposition, uses the following in-place algorithm:

$$\text{For } j = -1 \text{ to } -n : \begin{cases} \{\lambda_j, \gamma_j\} := \text{Split}\{\lambda_{j+1}\} \\ \gamma_j := \gamma_j - P\{\lambda_j\} \\ \lambda_j := \lambda_j + U\{\gamma_j\} \end{cases}$$

where $\tilde{P}(z)$ and $\tilde{U}(z)$ are the z-transforms of operator (P) and operator (U) respectively. A properties of lifting is that once the forward transform is obtained, the inverse can be immediately derived by reversing the ELS steps and toggle + and – operations.

The undecimated lifting wavelet transform (ULWT) does not subsample the input sequence $\lambda_0$ into even and odd sequences. Both undecimated Predict ($P_u$) and Update ($U_u$) operators with corresponding z-transforms $\tilde{P}_u(z)$ and $\tilde{U}_u(z)$ respectively, will be upsampled on a dyadic scale $k=2^{j-1}$ for decomposition at jth stage similar to traditional UWT:

$$\tilde{P}_u(z) = z^{-1}\tilde{P}(z) \text{ and } \tilde{U}_u(z) = z\tilde{U}(z)$$

Figure 5B:
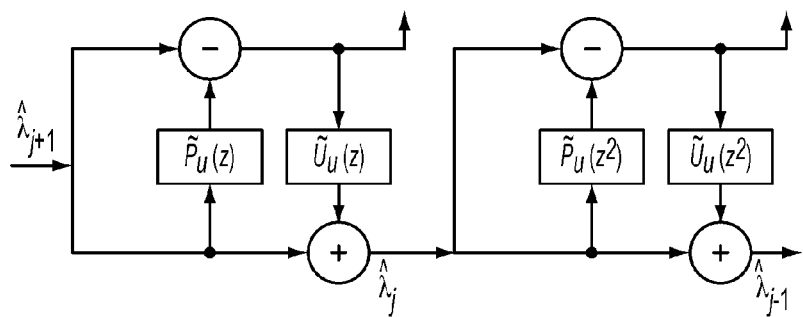

FIG. 5B shows the steps of the in-place algorithm for the undecimated lifting ULWT decomposition:

$$\text{For } j = -1 \text{ to } -n : \begin{cases} \hat{\gamma}_{u,j} := \lambda_{j+1}, \lambda_{u,j} := \lambda_{j+1} \\ \hat{\gamma}_{u,j} := \hat{\gamma}_{u,j} - P_u\{\lambda_{u,j}\} \\ \lambda_{u,j} := \lambda_{u,j} + U_u\{\hat{\gamma}_{u,j}\} \end{cases}$$

where $\lambda_{j+1}$ is signal approximation into the jth stage. Similar to LWT, the inverse ULWT is performed by reversing the ELS steps and toggle + and – operations.

When using ECG in automated medical analysis, there must be reliable detection of the fiducial waves: the QRS complexes, P and T waves. The detection process has many challenges: baseline wandering and noise artifacts, irregular morphology of the waveforms, and frequency overlapping among the wide-band distribution of the characteristic waves. Very few algorithms work well for the detection of all fiducial points like ECG wave boundaries, the onsets and offsets of the P wave, T wave and the QRS complex.

The analysis of the ECG ST-segment involves three major parts which we describe in the following subsections: ST-Segment Detection, ST-Deviation measurement and ST-Episode Detection.

To identify the ST-segment in an ECG signal, accurate detection of the isoelectric line, the J point and the heart rate are required. The isoelectric line is the baseline of the electrocardiogram, typically measured between the T wave offset and the preceding P wave onset. It indicates no muscular activity in the heart at a particular point of time. This line is used as a reference to measure ST-segment deviation. The J point is the inflection point at which the QRS complex changes its direction of propagation. It occurs after the offset of the QRS point within a window of 20-50 samples at the rate of 250 Hz of sampling. The isoelectric point, the QRS offset and the J point are detected by discrete wavelet transform.

A single forward undecimated ULWT decomposition is implemented using lifted version of Daubechies D4. The level is determined based on the frequency sub-band to be extracted from the ECG signal. The transform is applied at the scales of 23 and 21. The isoelectric line is determined by approximating each beat with the 23 scale transform. A search method is used to find the most stable zero crossings between the P and T waves. This is obtained by using the windowing and backward search algorithms for the signal before the QRS complex. This is repeated for 20 beats and the average is determined as the isoelectric line. The J point is detected from the 21 scale transformation. This point corresponds to the peak after the S point. On estimating the J point, the ECG inflection point is determined on the denoised signal before applying transformation.

The ST-segment is defined as the part of the ECG signal between the J point and the onset of the T wave. This is achieved by the Windowing Technique. On the 21 scale, a windowed search is implemented from the S point. The region where the slope of the signal is maximum is determined and a backward search starts from the local maximum till the point where the signal is minimal. This point is fixed as the T onset. If there is no local maximum or minimum in the windowing technique, the T onset is estimated to be at the J+80 point.

From the detected J point and the ST-segment, the ST-deviation is measured. The ST-deviation is relative to a reference waveform for each subject. This reference level is computed from the first 30 seconds of the ECG data. The equation for the measurement is as follows:

$$ST \text{ Deviation} = [ST \text{ Level} - \text{Reference } ST \text{ level}]$$

ST level function is the measured difference between the isoelectric line and the ECG amplitude during the ST-segment at a given time. Reference ST level is the average ST level function during the first 30 seconds of the ECG. The equation calculates the ST-Deviation as the difference of the ST level and the Reference ST level. This ensures that any changes in the ST level due to unwanted factors such as noise, movement of the electrodes or patient, electrical axis shift and more importantly, non-ischemic ST changes are excluded. In the above formulation, if the ST deviation for a beat is greater than +0.1 mV then ST-Elevation is said to occur. If the ST deviation is less than −0.1 mV then ST-Depression is said to occur.

Figure 6:
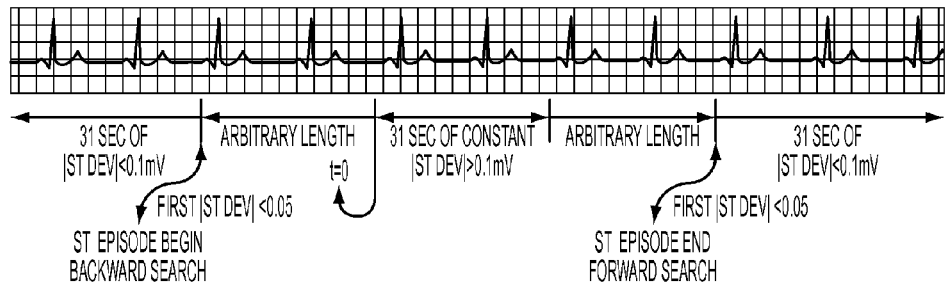
FIG. 6 illustrates the detection of an ST-episode.

Once the absolute value of the ST-deviation is found to be no less than 0.1 mV, the ST Episode detection begins. It involves a series of backward searches and forward searches from the critical point (see FIG. 6). The algorithm involves the following steps:

Interval Verification: Each episode lasts at least 30 seconds for which the absolute deviation is greater than 0.1 mV. A forward search for 30 seconds verifies this condition.

Episode Begin Annotation: A backward search takes place for the first beat occurrence with absolute deviation less than 0.05 mV and for which the previous 30 seconds have a absolute deviation less than 0.1 mV. This beat is annotated as 'Begin'.

Episode End Annotation: A forward search takes place for which the absolute ST deviation first exhibits less than 0.05 mV and for which the absolute deviation for next 30 seconds is less than 0.1 mV. This beat is annotated as 'End'.

Transient ST-segment episodes are the few time intervals during which an abnormal/crucial ST deviation is observed. As they occur as only a few bursts in time, they are called episodes. These episodes vary anywhere between one minute to several minutes and do not persist for hours together; hence they are termed as transient.

Apart from ST-segment depression, another type of Non-ST-Segment Elevation Myocardial Infarction (NSTEMI) may occur when there is no critical ST-segment deviation. In this case, however, the T wave may be small, flattened or inverted. Thus, the accuracy of the claimed system would increase when considering such relevant factors. A wavelet transforms is employed to identify the T point. The goal is to select a suitable choice of the wavelet decomposition scale and threshold setting to be able to detect low amplitude waves such as T-waves for various cases. Once the T point is detected, the QT interval can be further analyzed, as the Q point has already been detected from the QRS complex analysis discussed previously.

As discussed previously, a machine learning approach is applied to build an accurate coronary heart disease (CM) classifier. Recall that in the standard supervised learning framework, we are given a training set composed of n labeled training instances, $(x1, y1), (x2, y2), \ldots, (xm, yn,)$, where xi is the set of features representing instance i and yi is the corresponding class label. Given this training set, the goal is to learn a function that can accurately determine the class label of an unseen instance. When applying this learning framework to the CHD classification task, each xi represents a heart beat and yi is one of the six classes (later the class size will be increased) to which the beat belongs: N (normal), V (premature ventricular contraction), A (premature atrial contraction), F (fusion), R (right bundle branch block), and L (left bundle branch block). The goal is to learn from the training set a classifier that can accurately classify each heart beat as belonging to one of six classes.

Being an important problem, CHD classification has received a lot of attention in the bioinformatics community. In fact, the problem has been tackled extensively using machine learning approaches, primarily using the standard classification framework mentioned. On the other hand, we seek to improve CHD classification by examining the following important but largely unexplored research issues that can potentially address the inadequacies of the standard classification framework.

An issue that is largely ignored by the vast majority of existing work on CHD classification is the need for personalization. Specifically, the goal of many existing approaches is to train a classifier on manually classified heart beats collected from multiple people (e.g., those in the MIT-BIH Arrhythmia database) so that this "generic" CHD classifier can be applied to classify the heart beats of multiple people. The goal of the claimed invention however, is to build a model for predicting the heart beats of the person being monitored. Although a generic CHD classifier could still be used to make predictions for this person, prediction accuracy may be improved by building a personalized prediction model.

An embodiment of the invention is directed toward building a personalized CHD classifier, the issue being how to better exploit the "personal" heart beats collected from the person being monitored to train a personalized model? One simple option is to train a model on just these personal data samples. However, unless there are a sufficiently large number of personal samples, this model is unlikely to perform well due to the small size of the training set. Hence, the model can be trained on an augmented training set containing both these personal beats and the "standard" beats taken from existing databases (e.g., MIT-BIH).

There is a caveat, however. The augmented training set mentioned above is likely to contain a large number of standard beats and a small number of personal beats. Hence, the contribution of the personal beats to the construction of the model can be relatively small. To "magnify" the contribution of these personal beats, at least two options are explored. First, the number of standard beats is reduced by selecting only a subset of them for inclusion in the training set. The question is: which standard beats should be selected? In an embodiment of the invention, beats are taken from people who are similar to the person under monitoring in terms of personal, gender, age, and other biological factors, identifying these "similar" people by applying a clustering algorithm. Second, increasing the "importance" associated with the personal beats in the training set is explored. For example, many off-the-shelf learning algorithms allow one to adjust the cost of misclassifying an instance, and the misclassification cost associated with the personal beats can be increased.

The above discussion implicitly assumes that an expert is available for labeling the beats we collect from the person being monitored with the correct class. While it is not unrealistic to assume that such an expert is available, experiments with a setting where an expert is not available is also explored. Specifically, in this setting, all the personal beats are unlabeled, but these unlabeled beats are exploited since they may still convey useful information about the person being monitored. One option is to use to apply the model trained so far to automatically classify these unlabeled beats and use the automatically classified personal beats to train a personalized model. Another option is to apply semi-supervised learning algorithms such as semi-supervised EM and transductive learning to combine the labeled data (consisting of the standard beats) and the unlabeled data (consisting of the personal beats).

An embodiment of the invention is directed to the investigation of feature set incompatibility. Recall that when training a classifier using the records in standard databases, the features that can be exploited are limited to those that are available in the databases. In contrast, the features that can be collected from the person being monitored may not be identical to those provided in standard databases. To address this problem, a mixture model composed of two mixtures is acquired, one trained on the standard beats and the other on the personal beats.

As mentioned above, existing approaches to CHD classification are trained and evaluated on beats taken from standard databases. An implicit assumption underlying these approaches is that the training set is static (i.e., unchanged) with respect to time. Another rather undesirable assumption that these approaches commonly make is that the beats were collected independently of each other, essentially ignoring the observation that there might be some relationship between "nearby" beats (i.e., beats collected from the same person within a small timeframe) that can be profitably exploited to improve the performance of the classifier.

An embodiment of the invention is directed to a "time-aware" model for classifying CHD that can take into account issues involving the time dimension. One reason for building a time-aware model is practical: unlike many existing approaches, the current approach has to handle a continuously growing data set, as data are being collected from a person in real time. This means having to retrain the model from time to time so that recently collected data samples from the person can be accounted for. In addition, since the newly collected samples characterize the current condition of the person, they should be given more weight during the acquisition of the model. In other words, not only should more weight be given to the personal beats than the standard beats, more importance should also be placed on the recently collected personal beats than those collected previously.

Another, perhaps more important, reason for the time-aware model is that it involves interesting issues from a modeling perspective. Specifically, one critical time-related aspect that existing models fail to capture is trend. For instance, they fail to capture whether the person's body temperature or blood pressure has been rising or dropping during the previous k time steps. It is hypothesized that capturing these trends is as important as capturing the absolute values of these vital statistics at a particular point in time. One simple method would be to augment the representation of each feature: instead of having a feature value that simply reflects the data collected in the current time step, each feature value can be a sequence that is a concatenation of all the data collected for this feature in the previous k time steps.

While this simple method of concatenating feature values may work for discrete-valued features, it is conceivable that it may not work well for real-valued features. Consider a simple example where the values of a real-valued feature collected in the past three time steps is 1.2, 0.7, 0.9. If we concatenate these values using this simple method, it is possible that we may never see this feature value (i.e., 1.2#0.7#0.9) elsewhere in the training set due to data sparseness. Worse still, this representation does not capture the trend either: the learner will not be able to determine that the trend that the value drops and then rises.

To address this problem, a kernel is designed to compute the similarity between two time series, such that a high similarity value implies that the two time series have similar trends. Specifically, a time series is created by collecting data for a real-valued feature over time. In other words, there will be a one time series for each real-valued feature in each training instance. Now, to determine the similarity between two training instances (as is typically done in SVM training), the kernel is applied to each real-valued feature separately to compute the similarity of the corresponding time series, following which a composite kernel is used to combine the kernel values obtained from different real-valued features (as well as the kernel value(s) obtained from the discrete-valued features).

Of course, a natural question is: how can a kernel be designed to compute the similarity of two time series that can take into account the trends exhibited by them? The first method is cross correlation. In statistics, cross correlation is a method for measuring statistical relations, as measuring similarity of two random variables. In signal processing, cross correlation is used as a measure of the similarity of two signals as a function of a time-lag applied on one of the signals. An innate characteristic of this measure is identification of similar time series in volume, with consideration of time shifts. This characteristic is desirable to determine two time series that have similar trends as similar, even if one time series lags behind the other in the trends with respect to time.

The second method to consider is dynamic time wrapping (DTW), which also measures the similarity between two time series that may differ in time scale but are similar in shape. In speech recognition, this method is used to identify similar sounds between different speakers whose speech speed and pitch might be different. The algorithm defines a local cost matrix that returns the similarity value between any two points in the two time series. Given this cost matrix, DTW computes the lowest-cost alignment between the points in the two time series using a dynamic programming algorithm.

Since data is collected from the person being monitored in real time, the new data is used to (1) retrain the model from time to time to take into account the new data and (2) apply it in real time to classify the personal beats that are being collected at a fast rate. Hence, a model that can be (re)trained and applied efficiently is desirable. In addition, given that devices such as a smart phone have limited memory and processing power, a desirable device is one that is as small as possible without sacrificing accuracy.

Figure 7:
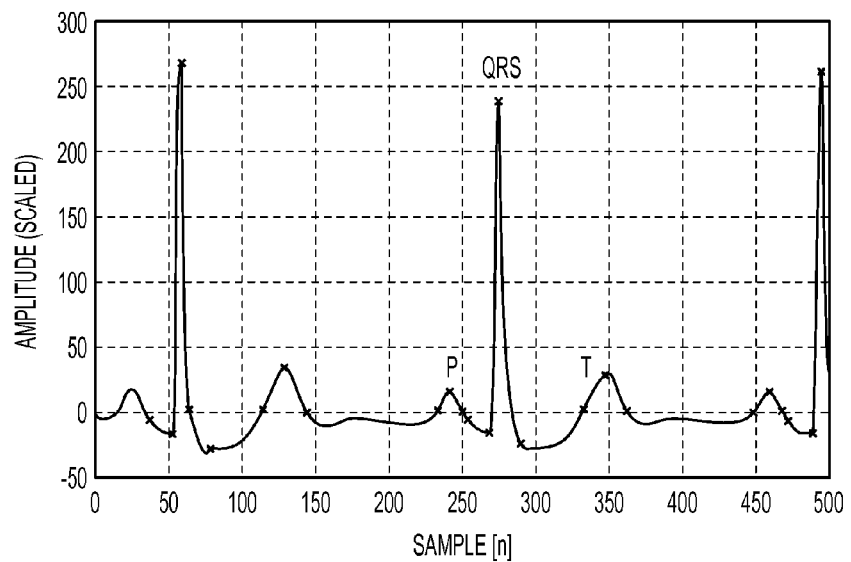
FIG. 7 shows an output of QRS-complex and PT fiducial points detectors using 11 characteristic points.

The claimed invention develops a system for the detection of ECG fiducial points. In certain embodiments the system is automated and in other embodiments, the detection of the ECG fiducal points is performed manually. The system provides two sets of outputs. The first output is the five characteristic points for the QRS-complex of each ECG heartbeat: Q, R and S, and the QRS onset and offset boundaries called PQ and J points. The second output is the six characteristic points: $P_{start}$, $P_{peak}$ and $P_{end}$ for P-wave, and $T_{start}$, $T_{peak}$ and $T_{end}$ for the T-wave. The system processing starts with buffer allocation of ECG samples over time window $\Delta t$ of 60 seconds. A normalized frequency of 250 Hz is selected for the buffered ECG signal. The ECG sensor signal must be resampled to this normalized frequency if it differs. FIG. 7 shows the 11-points detected in both the SQRS and SPT detectors for a typical ECG waveform: P-wave (onset, peak and offset), QRS-complex (PQ, Q, R, S, and J) and T-wave (onset, peak and offset).

ULWT reduced computation cost compared to basic FIR implementation as can be seen from comparing the Daubechies D4 UWT and ULWT implementation for the required number multiplication operations. For processing a 1 minute ECG segment at a sampling rate of 250 and for 7 decomposition stages, ULWT needs 420K operations compared to 840K operations for UWT.

What is claimed is:

1. A wearable sensor device for heart performance characterization and abnormality detection, comprising: an interface for receiving sampled data representing an electrical signal indicating electrical activity of a patient heart over a plurality of heart beat cycles; a signal processor for using the received sampled data in determining a first electrocardiogram morphological signal value and its discrete wavelet transformed (DWT) value over a plurality of heart cycles; a comparator for comparing the first electrocardiogram morphological signal value and its discrete wavelet transformed (DWT) value with a threshold value to provide a comparison indicator; a patient monitor that in response to said comparison indicator indicates a calculated signal value exceeding the threshold value, and generates an alert message associated with the threshold, a first module, wherein the first module provides data relating to measurement of change of an St-segment, QT interval or T wave and a second module, wherein the second module classifies heart beats as premature ventricular contraction, premature atrial contraction, fusion, right bundle branch block, left bundle branch block or normal using semi-supervised learning algorithms that are created from data derived from the patient's heart beats.

2. A device according to claim 1, wherein said signal processor uses the received sampled data in determining a second electrocardiogram morphological signal value and its discrete wavelet transformed (DWT) value over a plurality of heart cycles.

3. A device according to claim 2, wherein said signal processor determines a ratio of a first signal characteristic value to a second signal characteristic value.

4. A device according to claim 2, wherein said signal processor determines a relationship between the first electrocardiogram morphological signal and its discrete wavelet transformed (DWT) signal and the second morphological signal and its discrete wavelet transformed (DWT) signal.

5. The device according to claim 1, wherein the threshold value is a second electrocardiogram morphological signal and its discrete wavelet transformed (DWT) signal.

6. A device according to claim 5, wherein said comparator determines a comparison indicator indicating whether said at least one of the first or second signal values lies in a predetermined value range and said patient monitor, in response to said comparison indicator indicating a calculated signal value lies in a predetermined value range, generates an alert message associated with the value range.

7. A device according to claim 5, wherein said threshold value is derived from recorded electrical signal data for said patient.

8. A device according to claim 5, wherein said signal processor dynamically adjusts said threshold value in response to a determined sensitivity of arrhythmia detection.

9. A device according to claim 5, wherein said plurality of heart cycles are successive heart cycles.

10. A device according to claim 5, wherein said signal processor dynamically adjusts at least one of said predetermined threshold values in response to a determined heart electrical activity signal variation of said patient.

11. A device according to claim 1, including a repository of mapping information, associating ranges of said first and second signal values with corresponding medical conditions and said comparator compares said first and second characteristic values with said ranges to provide a comparison indicator identifying a medical condition and said patient monitor generates an alert message identifying said medical condition.

12. A device according to claim 11, wherein said predetermined mapping information associates ranges of said first and second signal values with particular patient demographic characteristics and with corresponding medical conditions and said system uses patient demographic data including at least one of, age weight, gender and height in comparing the first and second characteristic values with said ranges and generating an alert message indicating a potential medical condition.

13. A device according to claim 1, wherein said threshold value is derived from recorded electrical signal data for a population of patients.

14. A device according to claim 13, wherein said population of patients has similar demographic characteristics including at least two of, (a) age, (b) weight, (c) gender and (d) height, to those of said patient.

15. The device according to claim 1, wherein said alert message is delivered through a smartphone.

16. The device according to claim 1, wherein said alert message is computed by a smartphone.

* * * * *